US012595241B2

(12) United States Patent
Inoue et al.

(10) Patent No.: US 12,595,241 B2
(45) Date of Patent: Apr. 7, 2026

(54) METHOD OF PRODUCING PERFLUORO(2,4-DIMETHYL-2-FLUOROFORMYL-1,3-DIOXOLANE)

(71) Applicants: SAGAMI CHEMICAL RESEARCH INSTITUTE, Ayase (JP); TOSOH CORPORATION, Shunan (JP); TOSOH FINECHEM CORPORATION, Shunan (JP)

(72) Inventors: Munenori Inoue, Ayase (JP); Tatsuya Ueji, Ayase (JP); Hiroshi Matsuo, Shunan (JP)

(73) Assignees: SAGAMI CHEMICAL RESEARCH INSTITUTE, Ayase (JP); TOSOH CORPORATION, Shunan (JP); TOSOH FINECHEM CORPORATION, Shunan (JP)

( * ) Notice: Subject to any disclaimer, the term of this patent is extended or adjusted under 35 U.S.C. 154(b) by 922 days.

(21) Appl. No.: 17/766,116

(22) PCT Filed: Oct. 2, 2020

(86) PCT No.: PCT/JP2020/037576
§ 371 (c)(1),
(2) Date: Apr. 1, 2022

(87) PCT Pub. No.: WO2021/066155
PCT Pub. Date: Apr. 8, 2021

(65) Prior Publication Data

US 2023/0002342 A1 Jan. 5, 2023

(30) Foreign Application Priority Data

Oct. 4, 2019 (JP) ................................ 2019-183961

(51) Int. Cl.
*C07D 317/42* (2006.01)

(52) U.S. Cl.
CPC ................................ *C07D 317/42* (2013.01)

(58) Field of Classification Search
CPC ................................................... C07D 317/42
See application file for complete search history.

(56) References Cited

U.S. PATENT DOCUMENTS

| | | | | |
|---|---|---|---|---|
| 2,808,313 A * | 10/1957 | Herbert | .................. | C01D 17/00 423/196 |
| 3,308,107 A | 3/1967 | Selman | | |
| 3,321,517 A | 5/1967 | Selman | | |
| 3,404,162 A | 10/1968 | Selman | | |
| 3,450,716 A | 6/1969 | Selman | | |
| 3,467,702 A | 9/1969 | Selman | | |
| 3,475,456 A | 10/1969 | Selman | | |

FOREIGN PATENT DOCUMENTS

| | | | | |
|---|---|---|---|---|
| CN | 112638891 A | 4/2021 | | |
| EP | 0131810 A1 * | 6/1984 | | |
| FR | 1.422.169 | 12/1965 | | |
| GB | 1051647 | 12/1966 | | |
| GB | 1051648 A * | 12/1966 | ........... | C07D 317/42 |
| GB | 1051649 A * | 12/1966 | ........... | C07D 317/42 |
| GB | 1 560 842 A | 2/1980 | | |
| JP | 2013-75861 A | 4/2013 | | |
| JP | 2013-75863 A | 4/2013 | | |
| WO | WO 2020/050249 A1 | 3/2020 | | |
| WO | WO 2020/166632 A1 | 8/2020 | | |

OTHER PUBLICATIONS

Greco "Comprehensive Organic Chemistry Experiments for the Laboratory Classroom" 2017 translated from 2011 Portuguese language edition, edited by Carlos A M Afonso, RSC publishing, p. 61.*
Patrick, Graham Medicinal Chemistry, First Indian Reprint, 2015 Garland Science pp. 188-195.*
International Search Report issued Nov. 17, 2020 in PCT/JP2020/037576 filed Oct. 2, 2020, citing documents AA-AE, AO-AQ, and AY therein, 3 pages.
English translation of International Preliminary Report on Patentability and Written Opinion issued Apr. 14, 2022 in PCT/JP2020/037576, citing documents AA-AE, AO-AQ, and AY therein, 5 pages.
V. S. Yuminov, et al., "Perfluorinated dioxolanes. 1. Synthesis of perfluoro-4-oxo-1,3-dioxolane derivatives," Izvestiya Akademii Nauk SSSR, Seriya Khimicheskaya, 1988, pp. 392-395.
Combined Chinese Office Action and Search Report issued Dec. 27, 2023, in corresponding Chinese Patent Application No. 202080069713.7 (with English Translation) citing documents 15-17 therein, 19 pages.
Chinese Office Action issued Sep. 15, 2024 in Chinese Patent Application No. 202080069713.7 with English Machine translation, 13 pgs.
Extended European Search Report dated Oct. 2, 2023, issued in the corresponding European patent application No. 20871168.9, citing document 15 therein, 7 pages.
Chinese Office Action issued Nov. 29, 2024 in Chinese Patent Application No. 202080069713.7 (with English translation), 24 pages.

* cited by examiner

*Primary Examiner* — David K O'Dell
(74) *Attorney, Agent, or Firm* — Oblon, McClelland, Maier & Neustadt, L.L.P.

(57) ABSTRACT

Provided is a method of producing perfluoro(2,4-dimethyl-2-fluoroformyl-1,3-dioxolane, the method having a dimer reaction step of reacting a trifluoropyruvic acid fluoride dimer with hexafluoropropylene oxide in an organic solvent in the presence of one or more fluorides selected from the group consisting of potassium fluoride and sodium fluoride to obtain perfluoro(dimethyl-2-oxo-1,4-dioxane).

9 Claims, No Drawings

METHOD OF PRODUCING PERFLUORO(2,4-DIMETHYL-2-FLUORO-FORMYL-1,3-DIOXOLANE)

CROSS-REFERENCE TO RELATED APPLICATIONS

The present application is a 35 U.S.C. § 371 national stage patent application of International patent application PCT/JP2020/037576, filed on Oct. 2, 2020, which is based on and claims the benefits of priority to Japanese Application No. 2019-183961, filed on Oct. 4, 2019. The entire contents of these applications are incorporated herein by reference.

TECHNICAL FIELD

The present invention relates to a method of producing perfluoro(2,4-dimethyl-2-fluoroformyl-1,3-dioxolane).

BACKGROUND ART

Poly[perfluoro(2-methylene-4-methyl-1,3-dioxolane)] can be obtained by polymerizing perfluoro(2-methylene-4-methyl-1,3-dioxolane), which is derived from perfluoro(2,4-dimethyl-2-fluoroformyl-1,3-dioxolane). Poly[perfluoro(2-methylene-4-methyl-1,3-dioxolane)] is a polymer that is promising as a resin for gas separation membranes, a transparent resin for optical fibers, and the like. Methods of producing perfluoro(2,4-dimethyl-2-fluoroformyl-1,3-dioxolane), which is a raw material of the promising polymer, are disclosed in PTL 1 and PTL 2. In addition, NPL 1 describes a method of obtaining perfluoro(dimethyl-2-oxo-1,4-dioxane) by using, as a raw material, trifluoropyruvic acid fluoride dimer that is obtained by reacting hexafluoropropylene oxide and benzophenone (this production method is disclosed in PTL 3, for example).

PTL 1: U.S. Pat. No. 3,308,107

PTL 2: U.S. Pat. No. 3,404,162

PTL 3: UK Patent No. 1051647

NPL 1: Izvestiya Akademii Nauk SSSR, Seriya Khimicheskaya, pages 392 to 395, 1988

SUMMARY OF INVENTION

A production method disclosed in PTL 1 is a production method in which perfluoro(2,4-dimethyl-2-fluoroformyl-1,3-dioxolane) is obtained by using trifluoropyruvic acid fluoride as a raw material, reacting this raw material with hexafluoropropylene oxide in a diethylene glycol dimethyl ether solvent in the presence of cesium fluoride to obtain perfluoro(dimethyl-2-oxo-1,4-dioxane) as a synthetic intermediate, and then heating this synthetic intermediate in the presence of cesium fluoride. In addition, PTL 2 also discloses, as Example, a similar method of producing perfluoro(2,4-dimethyl-2-fluoroformyl-1,3-dioxolane), in which cesium fluoride is used. Meanwhile, NPL 1 describes a method of obtaining the above perfluoro(dimethyl-2-oxo-1,4-dioxane) by using a trifluoropyruvic acid fluoride dimer, which is obtained by reacting hexafluoropropylene oxide with benzophenone, as a raw material, and reacting this raw material with hexafluoropropylene oxide in a diethylene glycol dimethyl ether solvent in the presence of cesium fluoride.

However, cesium fluoride, which is used as a reagent in the methods disclosed in PTL 1 and 2 and the method described in NPL 1, is industrially valuable and is difficult to procure.

With this in mind, one aspect of the present invention provides for a method of producing perfluoro(2,4-dimethyl-2-fluoroformyl-1,3-dioxolane), in which a fluoride that is industrially inexpensive and can be easily procured is used as a reagent.

With regard to production of perfluoro(dimethyl-2-oxo-1,4-dioxane), which is an intermediate used for obtaining perfluoro(2,4-dimethyl-2-fluoroformyl-1,3-dioxolane), the trifluoropyruvic acid fluoride dimer that is used as a raw material in the method described in NPL 1 is a liquid at normal temperature and can be easily handled. As a result of diligent research, the present inventors found that perfluoro(2,4-dimethyl-2-fluoroformyl-1,3-dioxolane) could be produced using a step of obtaining perfluoro(dimethyl-2-oxo-1,4-dioxane) by reacting this trifluoropyruvic acid fluoride dimer with hexafluoropropylene oxide in an organic solvent in the presence of one or more fluorides selected from the group consisting of potassium fluoride and sodium fluoride.

That is, one aspect of the present invention is as follows.

[1] A method of producing perfluoro(2,4-dimethyl-2-fluoroformyl-1,3-dioxolane, the method having a dimer reaction step of reacting a trifluoropyruvic acid fluoride dimer with hexafluoropropylene oxide in an organic solvent in the presence of one or more fluorides selected from the group consisting of potassium fluoride and sodium fluoride to obtain perfluoro(dimethyl-2-oxo-1,4-dioxane).

[2] The method of producing perfluoro(2,4-dimethyl-2-fluoroformyl-1,3-dioxolane according to [1], wherein the organic solvent is one or more organic solvents selected from the group consisting of ethylene glycol dimethyl ether, diethylene glycol dimethyl ether, triethylene glycol dimethyl ether and tetraethylene glycol dimethyl ether.

[3] The method of producing perfluoro(2,4-dimethyl-2-fluoroformyl-1,3-dioxolane according to [1] or [2], wherein one or more fluorides selected from the group consisting of potassium fluoride and sodium fluoride is added at a quantity corresponding to 0.05 to 0.5 times the molar quantity of the trifluoropyruvic acid fluoride dimer in the dimer reaction step.

[4] The method of producing perfluoro(2,4-dimethyl-2-fluoroformyl-1,3-dioxolane according to any one of [1] to [3], wherein one or more fluorides selected from the group consisting of potassium fluoride and sodium fluoride is added at a quantity corresponding to 0.08 to 0.3 times the molar quantity of the trifluoropyruvic acid fluoride dimer in the dimer reaction step.

[5] The method of producing perfluoro(2,4-dimethyl-2-fluoroformyl-1,3-dioxolane according to any one of [1] to [4], wherein the dimer reaction step is carried out in the presence of potassium fluoride.

[6] The method of producing perfluoro(2,4-dimethyl-2-fluoroformyl-1,3-dioxolane according to any one of [1] to [5], the method having an isomerization step after the dimer reaction step.

[7] The method of producing perfluoro(2,4-dimethyl-2-fluoroformyl-1,3-dioxolane according to [6], wherein one or more fluorides selected from the group consisting of potassium fluoride and sodium fluoride is further added in the isomerization step.

[8] The method of producing perfluoro(2,4-dimethyl-2-fluoroformyl-1,3-dioxolane according to [7], wherein the quantity of the above fluoride further added in the isomerization step is a quantity corresponding to 0.1 to 2.0 times the molar quantity of the trifluoropyruvic acid fluoride dimer.

[9] The method of producing perfluoro(2,4-dimethyl-2-fluoroformyl-1,3-dioxolane according to [7] or [8], wherein the quantity of the above fluoride further added in the isomerization step is a quantity corresponding to 0.5 to 1.8 times the molar quantity of the trifluoropyruvic acid fluoride dimer.

[10] The method of producing perfluoro(2,4-dimethyl-2-fluoroformyl-1,3-dioxolane according to any one of [7] to [9], wherein the above fluoride further added in the isomerization reaction step is potassium fluoride.

[11] The method of producing perfluoro(2,4-dimethyl-2-fluoroformyl-1,3-dioxolane according to any one of [1] to [5], wherein the perfluoro(dimethyl-2-oxo-1,4-dioxane) obtained in the dimer reaction step is separated from the reaction liquid and then subjected to the isomerization step in the presence of an organic solvent and one or more fluorides selected from the group consisting of potassium fluoride and sodium fluoride.

[12] The method of producing perfluoro(2,4-dimethyl-2-fluoroformyl-1,3-dioxolane according to [11], wherein the organic solvent in the isomerization step is one or more organic solvents selected from the group consisting of ethylene glycol dimethyl ether, diethylene glycol dimethyl ether, triethylene glycol dimethyl ether and tetraethylene glycol dimethyl ether.

[13] The method of producing perfluoro(2,4-dimethyl-2-fluoroformyl-1,3-dioxolane according to [11] or [12], wherein the isomerization step is carried out in the presence of the above fluoride at a quantity corresponding to 0.1 to 2.0 times the molar quantity of the perfluoro(dimethyl-2-oxo-1,4-dioxane).

[14] The method of producing perfluoro(2,4-dimethyl-2-fluoroformyl-1,3-dioxolane according to any one of [11] to [13], wherein the isomerization step is carried out in the presence of the above fluoride at a quantity corresponding to 0.2 to 1.5 times the molar quantity of the perfluoro(dimethyl-2-oxo-1,4-dioxane).

[15] The method of producing perfluoro(2,4-dimethyl-2-fluoroformyl-1,3-dioxolane according to any one of [11] to [14], wherein the isomerization reaction step is carried out in the presence of potassium fluoride as the above fluoride.

[16] The method of producing perfluoro(2,4-dimethyl-2-fluoroformyl-1,3-dioxolane according to any one of [6] to [15], wherein one or more additives selected from the group consisting of crown ethers and fluorides is added in the isomerization step.

[17] The method of producing perfluoro(2,4-dimethyl-2-fluoroformyl-1,3-dioxolane according to any one of [6] to [10], wherein one or more additives selected from the group consisting of cesium fluoride and tetramethylammonium fluoride is added at a quantity corresponding to 0.05 to 0.2 times the molar quantity of the trifluoropyruvic acid fluoride dimer in the isomerization step.

[18] The method of producing perfluoro(2,4-dimethyl-2-fluoroformyl-1,3-dioxolane according to any one of [6] to [10], wherein 18-crown-6 or 15-crown-5 is added as an additive at a quantity corresponding to 0.05 to 1.5 times the molar quantity of the trifluoropyruvic acid fluoride dimer in the isomerization step.

[19] The method of producing perfluoro(2,4-dimethyl-2-fluoroformyl-1,3-dioxolane according to any one of [11] to [16], wherein one or more additives selected from the group consisting of cesium fluoride and tetramethylammonium fluoride is added in the isomerization step at a quantity corresponding to 0.03 to 0.15 times the molar quantity of perfluoro(dimethyl-2-oxo-1,4-dioxane) to be subjected to the reaction.

[20] The method of producing perfluoro(2,4-dimethyl-2-fluoroformyl-1,3-dioxolane according to any one of [11] to [16], wherein 18-crown-6 or 15-crown-5 is added as an additive in the isomerization step at a quantity corresponding to 0.05 to 1.0 times the molar quantity of perfluoro(dimethyl-2-oxo-1,4-dioxane) to be subjected to the reaction.

According to one aspect of the present invention, it is possible to provide a new method of producing perfluoro (2,4-dimethyl-2-fluoroformyl-1,3-dioxolane), in which potassium fluoride and/or sodium fluoride, which are fluorides that are industrially inexpensive and easy to procure, are used as reagents, and a trifluoropyruvic acid fluoride dimer, which is a liquid at normal temperature and is easy to handle, is used as a raw material.

DESCRIPTION OF EMBODIMENTS

One aspect of the present invention relates to a method of producing perfluoro(2,4-dimethyl-2-fluoroformyl-1,3-dioxolane) (hereinafter, also referred to simply as "the production method"). The above production method has a dimer reaction step of reacting the trifluoropyruvic acid fluoride dimer with hexafluoropropylene oxide in an organic solvent in the presence of one or more fluorides selected from the group consisting of potassium fluoride and sodium fluoride to obtain perfluoro(dimethyl-2-oxo-1,4-dioxane).

The above production method is a method of producing perfluoro(2,4-dimethyl-2-fluoroformyl-1,3-dioxolane). In the present invention and the present description, perfluoro (2,4-dimethyl-1,3-dioxolane-2-carboxylic acid) or alkali metal salts thereof are considered to be equivalent to perfluoro(2,4-dimethyl-2-fluoroformyl-1,3-dioxolane). In one embodiment, a product of the above production method mentioned above is perfluoro(2,4-dimethyl-2-fluoroformyl-1,3-dioxolane), perfluoro(2,4-dimethyl-1,3-dioxolane-2-carboxylic acid), an alkali metal salt of perfluoro(2,4-dimethyl-1,3-dioxolane-2-carboxylic acid), or a mixture of two of these or three or more of these.

The above production method will be explained in greater detail below.

In the above production method, perfluoro(dimethyl-2-oxo-1,4-dioxane), which is an intermediate used for producing perfluoro(2,4-dimethyl-2-fluoroformyl-1,3-dioxolane), can be obtained by, for example, charging a pressure-resistant vessel with the trifluoropyruvic acid fluoride dimer, an organic solvent and potassium fluoride and/or sodium fluoride, cooling, and then adding and reacting hexafluoropropylene oxide. Next, perfluoro(2,4-dimethyl-2-fluoroformyl-1,3-dioxolane) can be obtained by, for example, increasing the temperature and subjecting the compound to an isomerization step. In addition, it is possible to subject the perfluoro(dimethyl-2-oxo-1,4-dioxane), which is an intermediate used for producing perfluoro(2,4-dimethyl-2-fluoroformyl-1,3-dioxolane), to a dimer reaction step, separating by means of a separation procedure such as extraction separation or distillation separation, and then carry out the isomerization step. The fluoride used in the dimer reaction step is one or more fluorides selected from the group consisting of potassium fluoride and sodium fluoride. Potassium fluoride and sodium fluoride are industrially inexpensive and can be easily procured. Meanwhile, it has been said that potassium fluoride and sodium fluoride are less reactive in reactions than cesium fluoride, as described in, for example, Organic Letters, 2010, 12, 3740 to 3743, and the like. On the contrary, as a result of diligent research, the present inventors discovered a new reaction system in which potassium fluoride and/or sodium fluoride, which had lower activity in conventional reactions, had high activity. This matter is discussed later. The one or more fluorides selected from the group consisting of potassium fluoride and sodium fluoride may be only potassium fluoride, only sodium fluoride, or a combination of potassium fluoride and sodium fluoride. In the present description, "potassium fluoride and/or sodium fluoride" means any of only potassium fluoride, only sodium fluoride or a combination of potassium fluoride and sodium fluoride.

The trifluoropyruvic acid fluoride dimer used in the above production method can be obtained at a high yield from hexafluoropropylene oxide by using conditions disclosed in, for example, the specification of UK Patent No. 1051647 (PTL 3). In addition, a commercially available product may be used as the trifluoropyruvic acid fluoride dimer.

An example of the trifluoropyruvic acid fluoride dimer is 4-fluoro-5-oxo-2,4-bis(trifluoromethyl)-1,3-dioxolane-2-carbonyl fluoride. 4-fluoro-5-oxo-2,4-bis(trifluoromethyl)-1,3-dioxolane-2-carbonyl fluoride can be represented by formula 1 below.

(Formula 1)

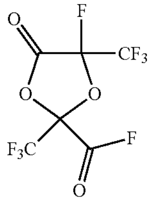

The organic solvent is not particularly limited as long as the solvent is inert in the reaction. Examples of the organic solvent include aromatic solvents such as toluene, ethylbenzene, xylene and mesitylene; and ether-based solvents such as ethylene glycol dimethyl ether, diethylene glycol dimethyl ether (also known as diglyme), triethylene glycol dimethyl ether and tetraethylene glycol dimethyl ether. It is possible to use only one organic solvent or two or more organic solvents mixed at arbitrary proportions. From the perspective of solubility of the potassium fluoride and/or sodium fluoride used, the organic solvent is preferably an ether-based solvent such as ethylene glycol dimethyl ether, diethylene glycol dimethyl ether, triethylene glycol dimethyl ether and tetraethylene glycol dimethyl ether, or two or more of the ether-based solvents mixed at arbitrary proportions, with diethylene glycol dimethyl ether being particularly preferred. The usage quantity of the organic solvent in the dimer reaction step is not particularly limited, and the organic solvent can generally be used at a quantity corresponding to 0.3 to 5.0 times the mass of the trifluoropyruvic acid fluoride dimer to be subjected to the reaction. It is preferable for the amount of moisture in the reaction system to be low in order for the reaction to progress favorably. Specifically, the amount of moisture in the reaction system in the dimer reaction step is preferably 500 ppm or less, more preferably 100 ppm or less, and further preferably 50 ppm or less. Units mentioned in the present description (ppm) are on a mass basis.

In the above production method, the potassium fluoride and sodium fluoride can be commercially available anhydrous products, spray dried products or hydrates. In addition, these may be used in a form obtained by supporting on calcium fluoride or the like. From the perspective of improving yield, use of potassium fluoride is preferred, and use of anhydrous or spray dried potassium fluoride is more preferred.

The usage quantity of the fluoride in the dimer reaction step can fall within the range of, for example, 0.05 to 1.5 times the molar quantity of the trifluoropyruvic acid fluoride dimer to be subjected to the reaction. The reaction progresses slowly if this usage quantity is too low, and the yield may decrease, which is not economically advantageous, if this usage quantity is high. From the perspectives mentioned above, the usage quantity of the above fluoride in the dimer reaction step, in one embodiment, is preferably 0.05 to 1.2 times the molar quantity of the trifluoropyruvic acid fluoride dimer to be subjected to the reaction, more preferably 0.05 to 0.8 times this molar quantity, further preferably 0.05 to 0.5 times this molar quantity, further preferably 0.07 to 0.4 times this molar quantity, and particularly preferably 0.08 to 0.3 times this molar quantity. In addition, the usage quantity of the above fluoride in the dimer reaction step can be, in one embodiment, 0.1 to 1.2 times this molar quantity or 0.1 to 0.8 times this molar quantity. In a case where potassium fluoride and sodium fluoride are used as fluorides, the usage quantity of the above fluorides is the total usage quantity thereof. This is also true for other quantities relating to the above fluorides in the present invention and the present description. Use of potassium fluoride as the fluoride is preferred in the dimer reaction step, and in this case, the quantity of potassium fluoride used is such that a molar quantity relative to the trifluoropyruvic acid dimer can be used as a preferred usage quantity.

The usage quantity of hexafluoropropylene oxide in the dimer reaction step can theoretically be a quantity corresponding to 2.0 times or more the molar quantity of the trifluoropyruvic acid fluoride dimer to be subjected to the reaction, and from the perspective of improving the yield, it is generally preferable for this usage quantity to be 1.9 to 2.8 times this molar quantity. In addition, a quantity corresponding to 1.9 to 2.5 times this molar quantity can be used in one aspect.

An example of a manner of addition of components in the dimer reaction step involves adding a mixture of the trifluoropyruvic acid fluoride dimer, potassium fluoride and/or sodium fluoride and an organic solvent at a temperature within the range −30° C. to 60° C. After the addition of the hexafluoropropylene oxide, a temperature within this range may be maintained for a period of 2 hours to 48 hours in order to complete the production of perfluoro(dimethyl-2-oxo-1,4-dioxane) in the dimer reaction step. The temperature mentioned in the present description is the temperature of the reaction liquid unless explicitly stated otherwise.

In the above production method, it is possible to produce the perfluoro(dimethyl-2-oxo-1,4-dioxane), which is an intermediate used for producing perfluoro(2,4-dimethyl-2-fluoroformyl-1,3-dioxolane), by carrying out the dimer reaction step. After the dimer reaction step, the above production method may have an isomerization step of isomerizing the obtained perfluoro(dimethyl-2-oxo-1,4-dioxane) into perfluoro(2,4-dimethyl-2-fluoroformyl-1,3-dioxolane). For example, in the isomerization step, the reaction liquid after the dimer reaction step is reacted for a period of 4 hours to 72 hours at a temperature of 100° C. to 150° C. so as to enable the isomerization reaction to progress and complete. The isomerization reaction is preferably carried out in a pressure-resistant vessel.

The one or more fluorides selected from the group consisting of potassium fluoride and sodium fluoride may also be added in the isomerization step. In this case, the quantity of above fluoride added in the dimer reaction step and the isomerization step is, in one embodiment, preferably a quantity corresponding to 0.1 to 2.0 times the molar quantity of trifluoropyruvic acid fluoride dimer (specifically, the quantity of trifluoropyruvic acid fluoride dimer charged in the dimer reaction step), more preferably 0.5 to 1.8 times this molar quantity, and further preferably 1.0 to 1.6 times this molar quantity. In addition, the quantity of the above fluoride added in the dimer reaction step and the isomerization step can be, in one embodiment, a quantity corresponding to 0.05 to 0.7 times the molar quantity of the trifluoropyruvic acid fluoride dimer (specifically, the quantity of the trifluoropyruvic acid fluoride dimer charged in the dimer reaction step). By adding the above fluoride in multiple portions in this way, the yield of perfluoro(2,4-dimethyl-2-fluoroformyl-1,3-dioxolane) may be improved. In addition, the fluoride that is further added in the isomerization step is more preferably potassium fluoride from the perspective of achieving a high perfluoro(2,4-dimethyl-2-fluoroformyl-1,3-dioxolane) yield. The concentration of the above fluoride relative to the organic solvent is not particularly limited, and from the perspective of improving the yield, this concentration is preferably 1 mass % to 30 mass % in the isomerization step.

In addition, it is possible to carry out a reaction with additive(s) also present in the isomerization step in order to improve the reactivity of the above fluoride. By using additive(s), the yield of perfluoro(2,4-dimethyl-2-fluoroformyl-1,3-dioxolane) can be improved and/or the usage quantity of the one or more fluorides selected from the group consisting of potassium fluoride and sodium fluoride can be reduced. Examples of additives able to be used include crown ethers such as 18-crown-6 and 15-crown-5; fluorides such as cesium fluoride and tetramethylammonium fluoride; polyetheramines such as tris[2-(2-methoxyethoxy)ethyl] amine (TDA-1); and polar solvents such as dimethylformamide and dimethyl sulfoxide. Use of cesium fluoride is particularly preferred. That is, use of cesium fluoride and at least one of sodium fluoride and potassium fluoride is preferred in the isomerization step, and use of potassium fluoride and cesium fluoride is more preferred. In a case where an additive is one or more from among crown ethers and polyetheramines, the usage quantity of the additive can be a quantity corresponding to 0.05 to 1.5 times the molar quantity of the trifluoropyruvic acid fluoride dimer (specifically, the quantity of the trifluoropyruvic acid fluoride dimer charged in the dimer reaction step). In addition, in a case where an additive is one or more from among fluorides, the usage quantity of the additive is preferably a quantity corresponding to 0.02 to 0.5 times the molar quantity of the trifluoropyruvic acid fluoride dimer (specifically, the quantity of the trifluoropyruvic acid fluoride dimer charged in the dimer reaction step), more preferably 0.03 to 0.3 times this molar quantity, and further preferably 0.05 to 0.2 times this molar quantity. In addition, the usage quantity of the fluoride used as an additive is preferably a quantity corresponding to 0.05 to 1.0 times the total molar quantity of the one or more fluorides selected from the group consisting of potassium fluoride and sodium fluoride used in the isomerization step (specifically, the total quantity of the one or more fluorides selected from the group consisting of potassium fluoride and sodium fluoride used in the dimer reaction step and the one or more fluorides selected from the group consisting of potassium fluoride and sodium fluoride used in the isomerization step), and more preferably 0.1 to 0.5 times this total molar quantity. The time at which to add the additive is not particularly limited, and from the perspective of improving the yield, it is preferable to add the additive at one or more stages selected from before and during the isomerization step. Cesium fluoride is industrially valuable, as mentioned before, but potassium fluoride and/or sodium fluoride, which are industrially inexpensive and can be easily procured, can be used as reagents in the dimer reaction step in the above production method. Therefore, even if cesium fluoride is used as an additive, the above production method can be industrially advantageous compared to the conventional production methods mentioned above in which cesium fluoride is used.

In the above production method, after the dimer reaction step, it is possible to subject the perfluoro(dimethyl-2-oxo-1,4-dioxane), which is an intermediate used for producing perfluoro(2,4-dimethyl-2-fluoroformyl-1,3-dioxolane), to separation by means of a separation procedure such as extraction separation or distillation separation, and then carry out the isomerization step. In this case, the separated perfluoro(dimethyl-2-oxo-1,4-dioxane) can be reacted in the presence of an organic solvent and one or more fluorides selected from the group consisting of potassium fluoride and sodium fluoride. With regard to organic solvents in the isomerization step, it is possible to refer to earlier descriptions relating to organic solvents in the dimer reaction step. It is preferable for the amount of moisture in the reaction system to be low in order for the reaction to progress favorably. Specifically, the amount of moisture in the reaction system in the isomerization step is preferably 500 ppm or less, more preferably 100 ppm or less, and further preferably 50 ppm or less. The usage quantity of the one or more fluorides selected from the group consisting of potassium fluoride and sodium fluoride is preferably a quantity corresponding to 0.1 to 2.0 times the molar quantity of perfluoro(dimethyl-2-oxo-1,4-dioxane), and more preferably 0.2 to 1.5 times this molar quantity. In addition, the fluoride present is more preferably potassium fluoride from the perspective of achieving a high perfluoro(dimethyl-2-oxo-1,4-dioxane) yield. The concentration of the fluoride relative to the organic solvent in this case is not particularly limited, and from the perspective of improving the yield, this concentration is preferably 1 mass % to 30 mass %.

In addition, it is possible to carry out a reaction with additive(s) also present in the isomerization step in order to improve the reactivity of the fluoride. By using additive(s), the yield of perfluoro(2,4-dimethyl-2-fluoroformyl-1,3-dioxolane) can be improved and/or the usage quantity of the one or more fluorides selected from the group consisting of potassium fluoride and sodium fluoride can be reduced. Examples of additives able to be used include crown ethers such as 18-crown-6 and 15-crown-5; fluorides such as cesium fluoride and tetramethylammonium fluoride; polyetheramines such as tris[2-(2-methoxyethoxy)ethyl] amine (TDA-1); and polar solvents such as dimethylformamide and dimethyl sulfoxide. Use of cesium fluoride is particularly preferred. That is, use of cesium fluoride and at least one selected from the group consisting of sodium fluoride and potassium fluoride is preferred in the isomerization step, and use of potassium fluoride and cesium fluoride is more preferred. In a case where an additive is selected from crown ethers and polyetheramines, the usage quantity of the additive can be a quantity corresponding to 0.05 to 1.0 times the molar quantity of the perfluoro(dimethyl-2-oxo-1,4-dioxane) being reacted. In addition, in a case where an additive is a fluoride, the usage quantity of the additive is preferably a quantity corresponding to 0.01 to 0.30 times the molar quantity of the perfluoro(dimethyl-2- oxo-1,4-dioxane) to be subjected to the reaction, more preferably 0.02 to 0.20 times this molar quantity, and particularly preferably 0.03 to 0.15 times this molar quantity. In addition, the usage quantity of the fluoride being used as an additive is preferably a quantity corresponding to 0.05 to 1.0 times the molar quantity of the one or more fluorides selected from the group consisting of potassium fluoride and sodium fluoride used in the isomerization step, and more preferably 0.1 to 0.5 times this total molar quantity.

The perfluoro(dimethyl-2-oxo-1,4-dioxane) obtained in the dimer reaction step, which is a synthetic intermediate used for producing perfluoro(2,4-dimethyl-2-fluoroformyl-1,3-dioxolane), can be perfluoro(3,5-dimethyl-2-oxo-1,4-dioxane) represented by formula 2 or perfluoro(3,6-dimethyl-2-oxo-1,4-dioxane) represented by formula 3, and may be a mixture of these diastereomers. In addition, the perfluoro(dimethyl-2-oxo-1,4-dioxane) obtained in the dimer reaction step may be a composition of these isomers.

(Formula 2)

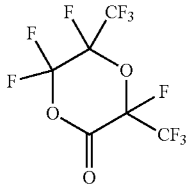

(Formula 3)

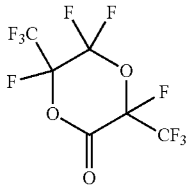

By cooling to room temperature, depressurizing, filtering and then separating and removing the upper organic solvent layer as a post-treatment after the isomerization step, it is possible to obtain the target perfluoro(2,4-dimethyl-2-fluoroformyl-1,3-dioxolane). In addition, the target product can be obtained by distilling the reaction mixture. Room temperature means a temperature within a range of, for example, 20° C. to 25° C.

From the perspective of further improving the yield of perfluoro(2,4-dimethyl-2-fluoroformyl-1,3-dioxolane), preferred embodiments of the above production method are as follows.

In one embodiment, potassium fluoride is used as a fluoride in the dimer reaction step, the usage quantity of potassium fluoride is a quantity corresponding to 0.05 to 1.2 times the molar quantity of the trifluoropyruvic acid fluoride dimer, potassium fluoride is further added in the isomerization step, and the quantity of potassium fluoride added is preferably a quantity corresponding to 0.1 to 2.0 times the molar quantity of the trifluoropyruvic acid fluoride dimer.

In one embodiment, potassium fluoride is used as a fluoride in the dimer reaction step, the usage quantity of potassium fluoride is a quantity corresponding to 0.05 to 0.5 times the molar quantity of the trifluoropyruvic acid fluoride dimer, potassium fluoride is further added in the isomerization step, and the quantity of potassium fluoride added is preferably a quantity corresponding to 0.5 to 1.8 times the molar quantity of the trifluoropyruvic acid fluoride dimer.

In one embodiment, potassium fluoride is used as a fluoride in the dimer reaction step, the usage quantity of potassium fluoride is a quantity corresponding to 0.08 to 0.3 times the molar quantity of the trifluoropyruvic acid fluoride dimer, potassium fluoride is further added in the isomerization step, and the quantity of potassium fluoride added is preferably a quantity corresponding to 1.0 to 1.8 times the molar quantity of the trifluoropyruvic acid fluoride dimer.

In one embodiment, potassium fluoride is used as a fluoride in the dimer reaction step, the usage quantity of potassium fluoride is a quantity corresponding to 0.05 to 1.2 times the molar quantity of the trifluoropyruvic acid fluoride dimer, potassium fluoride and cesium fluoride are both added in the isomerization step, the quantity of potassium fluoride added is preferably a quantity corresponding to 0.1 to 2.0 times the molar quantity of the trifluoropyruvic acid fluoride dimer, and the quantity of cesium fluoride added is preferably a quantity corresponding to 0.02 to 0.5 times the molar quantity of perfluoro(dimethyl-2-oxo-1,4-dioxane).

In one embodiment, potassium fluoride is used as a fluoride in the dimer reaction step, the usage quantity of potassium fluoride is a quantity corresponding to 0.05 to 0.5 times the molar quantity of the trifluoropyruvic acid fluoride dimer, potassium fluoride and cesium fluoride are both added in the isomerization step, the quantity of potassium fluoride added is preferably a quantity corresponding to 0.5 to 1.8 times the molar quantity of the trifluoropyruvic acid fluoride dimer, and the quantity of cesium fluoride added is preferably a quantity corresponding to 0.03 to 0.3 times the molar quantity of perfluoro(dimethyl-2-oxo-1,4-dioxane).

In one embodiment, potassium fluoride is used as a fluoride in the dimer reaction step, the usage quantity of potassium fluoride is a quantity corresponding to 0.08 to 0.3 times the molar quantity of the trifluoropyruvic acid fluoride dimer, potassium fluoride and cesium fluoride are both added in the isomerization step, the quantity of potassium fluoride added is preferably a quantity corresponding to 1.0 to 1.8 times the molar quantity of the trifluoropyruvic acid fluoride dimer, and the quantity of cesium fluoride added is preferably a quantity corresponding to 0.05 to 0.2 times the molar quantity of perfluoro(dimethyl-2-oxo-1,4-dioxane).

The perfluoro(2,4-dimethyl-2-fluoroformyl-1,3-dioxolane) obtained by the above production method can be derived into perfluoro(2-methylene-4-methyl-1,3-dioxolane) using a method disclosed in, for example, the description of U.S. Pat. No. 3,308,107 (PTL 1). In addition, this perfluoro(2,4-dimethyl-2-fluoroformyl-1,3-dioxolane) can be converted into perfluoro(2-methylene-4-methyl-1,3-dioxolane) using a synthesis method shown in formula 4 below, which is described in Macromolecules 2005, vol. 38, pages 4237 to 4245. That is, perfluoro(2-methylene-4-methyl-1,3-dioxolane) can be produced by hydrolyzing perfluoro(2,4-dimethyl-2-fluoroformyl-1,3-dioxolane) to obtain potassium perfluoro(2,4-dimethyl-1,3-dioxolane-2-carboxylate) and then carrying out a decarboxylation reaction. The perfluoro(2,4-dimethyl-1,3-dioxolane-2-carboxylic acid) or alkali metal salt thereof is a synthetic intermediate used for producing perfluoro(2,4-dimethyl-2-fluoroformyl-1,3-dioxolane) from perfluoro(2,4-dimethyl-2-fluoroformyl-1,3-dioxolane). As mentioned above, these are equivalent to perfluoro(2,4-dimethyl-2-fluoroformyl-1,3-dioxolane) in the present invention and the present description.

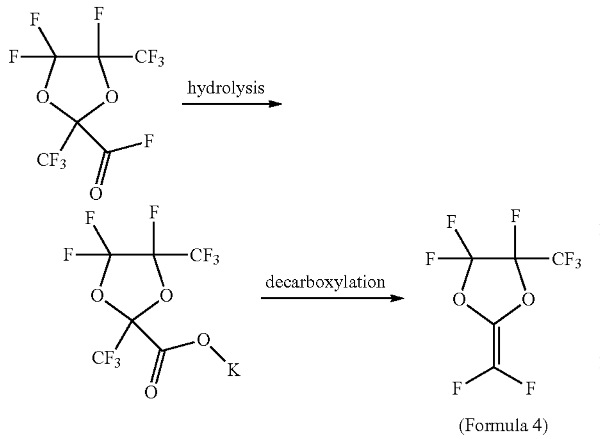

(Formula 4)

The above production method may also have a dimer synthesis step of synthesizing a trifluoropyruvic acid fluoride dimer before the dimer reaction step. An example of a reaction carried out in the dimer synthesis step is a reaction between benzophenone and hexafluoropropylene oxide disclosed in, for example, the description of UK Patent No. 1051647 (PTL 3).

EXAMPLES

The present invention will be explained below in further detail through Examples. However, the present invention is in no way limited to the embodiments shown in Examples.

The following apparatus was used in the analysis below.

$^{19}F$ NMR: BRUKER AVANCE II 400

Reference Example 1

Preparation of Trifluoropyruvic Acid Fluoride Dimer

Benzophenone (3.19 kg, 18 mol) was charged in a stirrer-equipped SUS316 10 L autoclave having a pressure resistance of 8 MPa and cooled to 0° C. using an ice bath, after which hexafluoropropylene oxide (3.15 kg, 19 mol) was added thereto.

Next, the autoclave was sealed, the reaction mixture was heated to 185° C. while being stirred, and a reaction was carried out for 4 hours.

Following completion of the reaction, the system was cooled to room temperature, and liquid separation was carried out to obtain trifluoropyruvic acid fluoride dimer (a clear pale yellow liquid, 2.06 kg). In quantitative determination by $^{19}F$ NMR using benzotrifluoride as an internal standard substance, 1.82 kg (6.3 mol) of the target trifluoropyruvic acid fluoride dimer was produced (a yield of 72% relative to benzophenone). The obtained product was a mixture of two diastereomers, and the ratio of these was 1/1 (in terms of molar ratio). $^{19}F$ NMR (neat, 376 MHz) (Isomer 1) δ22.4, -81.4, -81.8, -122.9, (Isomer 2) δ22.3, -81.7, -81.8, -122.1.

Example 1

Potassium fluoride (0.195 g, 3.4 mmol; 0.7 times the molar quantity of trifluoropyruvic acid fluoride dimer) was added to a 25 mL test tube made of FEP (a tetrachloroethylene-hexafluoropropylene copolymer), a rubber septum was attached, depressurization/argon purging was carried out 3 times, and diethylene glycol dimethyl ether (1.90 g, 14 mmol) and trifluoropyruvic acid fluoride dimer (1.40 g, 4.9 mmol) were added. In an argon atmosphere, the FEP test tube was cooled to 0° C. using an ice bath and connected to a balloon containing hexafluoropropylene oxide (1.83 g, 11 mmol) while being stirred. Next, stirring was then carried out for 36 hours in a cooling bath at a temperature of −20° C. After allowing the obtained solution to rest at room temperature, the upper layer (2.47 g) was subjected to NMR analysis by means of $^{19}F$ NMR using benzotrifluoride as an internal standard substance, and it was confirmed that 0.164 g of perfluoro(dimethyl-2-oxo-1,4-dioxane) (a yield of 6% relative to the trifluoropyruvic acid fluoride dimer) had been produced. The lower layer (2.64 g) was subjected to NMR analysis by means of $^{19}F$ NMR using benzotrifluoride as an internal standard substance, and it was confirmed that 0.27 g of perfluoro(dimethyl-2-oxo-1,4-dioxane) (a yield of 9% relative to the trifluoropyruvic acid fluoride dimer) had been produced (the combined yield of the upper layer and lower layer was 15% relative to the trifluoropyruvic acid fluoride dimer). It was confirmed that the perfluoro(dimethyl-2-oxo-1,4-dioxane) was produced as two diastereomers. $^{19}F$ NMR (376 MHz, $CDCl_3$) (Isomer 1) δ-81.6, -81.8, -82.2, -83.0, -117.2, -126.3. (Isomer 2) δ-81.6, -82.2, -83.0, -94.6, -113.7, -128.5.

Perfluoro(2,4-dimethyl-2-fluoroformyl-1,3-dioxolane) is produced by subjecting the thus obtained perfluoro(dimethyl-2-oxo-1,4-dioxane) to an isomerization step.

Example 2

Trifluoropyruvic acid fluoride dimer (1.47 g, 5.1 mmol), potassium fluoride (0.206 g, 3.6 mmol; 0.7 times the molar quantity of the trifluoropyruvic acid fluoride dimer; spray dried product) and diethylene glycol dimethyl ether (1.87 g, 14 mmol) were charged in a SUS316 30 mL autoclave having a pressure resistance of 10 MPa and cooled to 0° C. using an ice bath. Next, hexafluoropropylene oxide (1.90 g, 11 mmol) was introduced to the autoclave, and stirring was continued for 20 hours at a temperature of 0° C. After completion of the reaction, liquid phase was brought to at room temperature, the upper layer (2.81 g) was subjected to NMR analysis by means of $^{19}F$ NMR using benzotrifluoride as an internal standard substance, and 0.41 g of perfluoro (dimethyl-2-oxo-1,4-dioxane) (a yield of 13% relative to the trifluoropyruvic acid fluoride dimer) had been produced. The lower layer (2.15 g) was subjected to NMR analysis by means of $^{19}F$ NMR using benzotrifluoride as an internal standard substance, and it was confirmed that 0.29 g of perfluoro(dimethyl-2-oxo-1,4-dioxane) (a yield of 9% relative to the trifluoropyruvic acid fluoride dimer) had been produced (the combined yield of the upper layer and lower layer was 22% relative to the trifluoropyruvic acid fluoride dimer). It was confirmed that the perfluoro(dimethyl-2-oxo-1,4-dioxane) was produced as two diastereomers.

Perfluoro(2,4-dimethyl-2-fluoroformyl-1,3-dioxolane) is produced by subjecting the thus obtained perfluoro(dimethyl-2-oxo-1,4-dioxane) to an isomerization step.

Example 3

Trifluoropyruvic acid dimer (2.50 g, 8.7 mmol), potassium fluoride (54.4 mg, 0.94 mmol; 0.11 times the molar quantity of the trifluoropyruvic acid dimer; spray dried product) and diethylene glycol dimethyl ether (0.91 g, 6.8 mmol) were charged in a SUS316 30 mL autoclave having a pressure resistance of 10 MPa and cooled to 0° C. using an ice bath. Next, hexafluoropropylene oxide (4.0 g, 24.1 mmol) was introduced to the autoclave, and stirring was continued for 20 hours at a temperature of 0° C. After completion of the reaction, liquid phase was brought to at room temperature, the upper layer and lower layer were subjected to NMR analysis by means of $^{19}F$ NMR using benzotrifluoride as an internal standard substance, and it was confirmed that perfluoro(dimethyl-2-oxo-1,4-dioxane) (4.44 g, a yield of 82% relative to the trifluoropyruvic acid dimer) had been produced. It was confirmed that the perfluoro (dimethyl-2-oxo-1,4-dioxane) was produced as two diastereomers.

Example 4

A reaction was carried out under the same conditions as those used in Example 3, except that the quantity of potassium fluoride used was changed to 0.5 times the molar quantity of the trifluoropyruvic acid dimer, and it was confirmed that perfluoro(dimethyl-2-oxo-1,4-dioxane) was produced at a yield of 38% (relative to the trifluoropyruvic acid fluoride dimer).

Example 5

A reaction was carried out under the same conditions as those used in Example 3, except that the quantity of potassium fluoride used was changed to 0.05 times the molar quantity of the trifluoropyruvic acid dimer, and it was confirmed that perfluoro(dimethyl-2-oxo-1,4-dioxane) was produced at a yield of 42% (relative to the trifluoropyruvic acid fluoride dimer).

Example 6

Sodium fluoride (0.131 g, 3.1 mmol; 0.6 times the molar quantity of trifluoropyruvic acid dimer) was added to a 25 mL test tube made of FEP (a tetrachloroethylene-hexafluoropropylene copolymer), a rubber septum was attached, depressurization/argon purging was carried out 3 times, and diethylene glycol dimethyl ether (1.73 g, 12.9 mmol) and trifluoropyruvic acid dimer (1.5 g, 5.2 mmol) were added. In an argon atmosphere, the FEP test tube was cooled to 0° C. using an ice bath and connected to a balloon containing hexafluoropropylene oxide (1.73 g, 10.4 mmol) while being stirred. Next, stirring was then carried out for 36 hours in a cooling bath at a temperature of −20° C. The obtained solution was subjected to NMR analysis by means of $^{19}F$ NMR using benzotrifluoride as an internal standard substance, and it was confirmed that perfluoro(dimethyl-2-oxo-1,4-dioxane) (at a yield of 5% relative to the trifluoropyruvic acid dimer) had been produced. It was confirmed that the perfluoro(dimethyl-2-oxo-1,4-dioxane) was produced as two diastereomers.

Example 7

A stirrer, diethylene glycol dimethyl ether (2.70 g, 20.1 mmol), potassium fluoride (0.282 g, 4.85 mmol, 1.46 times the molar quantity of perfluoro(dimethyl-2-oxo-1,4-dioxane); spray dried product) and perfluoro(dimethyl-2-oxo-1,4-dioxane) (1.03 g, 3.32 mmol) were placed in an argon-purged 20 mL pressure-resistant tube, and the tube was then sealed. Stirring was carried out for 15 hours at a temperature of 130° C. After completion of the reaction, liquid phase was cooled to room temperature. Liquid separation was carried out to obtain an upper layer (a diglyme layer) and a lower layer (a fluorous layer). When the lower layer was subjected to NMR analysis by means of $^{19}F$ NMR using benzotrifluoride as an internal standard substance, it was confirmed that perfluoro(2,4-dimethyl-2-fluoroformyl-1,3-dioxolane) had been produced (0.68 g, a yield of 24% relative to perfluoro(dimethyl-2-oxo-1,4-dioxane). In addition, when the upper layer and unnecessary substances were dissolved in heavy water and subjected to NMR analysis by means of $^{19}F$ NMR using trifluoroethanol as an internal standard substance, it was confirmed that perfluoro(2,4-dimethyl-2-fluoroformyl-1,3-dioxolane) was produced as perfluoro(2,4-dimethyl-2-fluoroformyl-1,3-dioxolane) and perfluoro(2,4-dimethyl-1,3-dioxolane-2-carboxylic acid) and/or a potassium salt thereof (at a yield of 52% relative to perfluoro (dimethyl-2-oxo-1,4-dioxane)).

It was confirmed that the perfluoro(2,4-dimethyl-2-fluoroformyl-1,3-dioxolane) was produced as two diastereomers. $^{19}F$ NMR (376 MHz, $CDCl_3$) (Isomer 1) δ23.6, -77.8 (d,J=132 Hz), -80.1, -81.57, -83.56 (d,J=135 Hz), -124.9. (Isomer 2) δ23.2, -78.5 (d,J=132 Hz), -80.4, -81.6, -84.1 (d,J=139 Hz), -123.7. It was also confirmed that the perfluoro(2,4-dimethyl-1,3-dioxolane-2-carboxylic acid) and/or potassium salt thereof were produced as two diastereomers. $^{19}F$ NMR (376 MHz, $D_2O$) (Isomer 1) δ-78.8, -81.0, -81.9, -84.4, -124.8 . (Isomer 2) δ-79.5, -81.4, -82.0, -84.8, -124.9.

Example 8

A reaction was carried out under the same conditions as those used in Example 7, except that the quantity of potassium fluoride used was changed to 0.99 times the molar quantity of perfluoro(dimethyl-2-oxo-1,4-dioxane), and it was confirmed that perfluoro(2,4-dimethyl-2-fluoroformyl-1,3-dioxolane) was produced at a yield of 35% (relative to perfluoro(dimethyl-2-oxo-1,4-dioxane)) and perfluoro(2,4-dimethyl-1,3-dioxolane-2-carboxylic acid) and/or a potassium salt thereof were produced at a yield of 31% (relative to perfluoro(dimethyl-2-oxo-1,4-dioxane)). It was confirmed that the obtained compounds were each produced as two diastereomers.

Example 9

A reaction was carried out under the same conditions as those used in Example 7, except that the quantity of potassium fluoride used was changed to 1.0 times the molar quantity of perfluoro(dimethyl-2-oxo-1,4-dioxane) and the quantity of diethylene glycol dimethyl ether used was changed to 8.17 g (60.9 mmol), and it was confirmed that perfluoro(2,4-dimethyl-2-fluoroformyl-1,3-dioxolane) was produced at a yield of 36% (relative to perfluoro(dimethyl-2-oxo-1,4-dioxane)) and perfluoro(2,4-dimethyl-1,3-dioxolane-2-carboxylic acid) and/or a potassium salt thereof were produced at a yield of 38% (relative to perfluoro(dimethyl-2-oxo-1,4-dioxane)). It was confirmed that the obtained compounds were each produced as two diastereomers.

Example 10

A reaction was carried out under the same conditions as those used in Example 7, except that the quantity of potassium fluoride used was changed to 0.52 times the molar quantity of perfluoro(dimethyl-2-oxo-1,4-dioxane), and it was confirmed that perfluoro(2,4-dimethyl-2-fluoroformyl-1,3-dioxolane) was produced at a yield of 35% (relative to perfluoro(dimethyl-2-oxo-1,4-dioxane)) and perfluoro(2,4-dimethyl-1,3-dioxolane-2-carboxylic acid) and/or a potassium salt thereof were produced at a yield of 19% (relative to perfluoro(dimethyl-2-oxo-1,4-dioxane)). It was confirmed that the obtained compounds were each produced as two diastereomers.

Example 11

A reaction was carried out under the same conditions as those used in Example 7, except that the quantity of potassium fluoride used was changed to 0.88 times the molar quantity of perfluoro(dimethyl-2-oxo-1,4-dioxane) and cesium fluoride was used as an additive at a quantity corresponding to 0.09 times the molar quantity of perfluoro (dimethyl-2-oxo-1,4-dioxane), and it was confirmed that perfluoro(2,4-dimethyl-2-fluoroformyl-1,3-dioxolane) was produced at a yield of 42% (relative to perfluoro(dimethyl-2-oxo-1,4-dioxane)) and perfluoro(2,4-dimethyl-1,3-dioxolane-2-carboxylic acid) and/or a salt (a potassium salt and/or a cesium salt) thereof were produced at a yield of 49% (relative to perfluoro(dimethyl-2-oxo-1,4-dioxane)). It was confirmed that the obtained compounds were each produced as two diastereomers.

Example 12

A reaction was carried out under the same conditions as those used in Example 7, except that the quantity of potassium fluoride used was changed to 0.21 times the molar quantity of perfluoro(dimethyl-2-oxo-1,4-dioxane) and cesium fluoride was used as an additive at a quantity corresponding to 0.09 times the molar quantity of perfluoro (dimethyl-2-oxo-1,4-dioxane), and it was confirmed that perfluoro(2,4-dimethyl-2-fluoroformyl-1,3-dioxolane) was produced at a yield of 72% (relative to perfluoro(dimethyl-2-oxo-1,4-dioxane)) and perfluoro(2,4-dimethyl-1,3-dioxolane-2-carboxylic acid) and/or a salt (a potassium salt and/or a cesium salt) thereof were produced at a yield of 23% (relative to perfluoro(dimethyl-2-oxo-1,4-dioxane)). It was confirmed that the obtained compounds were each produced as two diastereomers.

Example 13

A reaction was carried out under the same conditions as those used in Example 7, except that the quantity of potassium fluoride used was changed to 0.25 times the molar quantity of perfluoro(dimethyl-2-oxo-1,4-dioxane) and cesium fluoride was used as an additive at a quantity corresponding to 0.05 times the molar quantity of perfluoro (dimethyl-2-oxo-1,4-dioxane), and it was confirmed that perfluoro(2,4-dimethyl-2-fluoroformyl-1,3-dioxolane) was produced at a yield of 63% (relative to perfluoro(dimethyl-2-oxo-1,4-dioxane)) and perfluoro(2,4-dimethyl-1,3-dioxolane-2-carboxylic acid) and/or a salt (a potassium salt and/or a cesium salt) thereof were produced at a yield of 24% (relative to perfluoro(dimethyl-2-oxo-1,4-dioxane)). It was confirmed that the obtained compounds were each produced as two diastereomers.

Example 14

A reaction was carried out under the same conditions as those used in Example 7, except that the fluoride used was sodium fluoride, sodium fluoride was added at a quantity corresponding to 0.21 times the molar quantity of perfluoro (dimethyl-2-oxo-1,4-dioxane) and cesium fluoride was used as an additive at a quantity corresponding to 0.10 times the molar quantity of perfluoro(dimethyl-2-oxo-1,4-dioxane), and it was confirmed that perfluoro(2,4-dimethyl-2-fluoroformyl-1,3-dioxolane) was produced at a yield of 62% (relative to perfluoro(dimethyl-2-oxo-1,4-dioxane)) and perfluoro(2,4-dimethyl-1,3-dioxolane-2-carboxylic acid) and/or a salt (a sodium salt and/or a cesium salt) thereof were produced at a yield of 8% (relative to perfluoro(dimethyl-2-oxo-1,4-dioxane)). It was confirmed that the obtained compounds were each produced as two diastereomers.

Example 15

A reaction was carried out under the same conditions as those used in Example 7, except that the quantity of potassium fluoride used was changed to 0.10 the molar quantity of perfluoro(dimethyl-2-oxo-1,4-dioxane), and tetramethylammonium fluoride was added as an additive at a quantity corresponding to 0.10 times the molar quantity of perfluoro (dimethyl-2-oxo-1,4-dioxane), and it was confirmed that perfluoro(2,4-dimethyl-2-fluoroformyl-1,3-dioxolane) was produced at a yield of 50% (relative to perfluoro(dimethyl-2-oxo-1,4-dioxane)). It was confirmed that the obtained compound was produced as two diastereomers.

Example 16

Trifluoropyruvic acid fluoride dimer (6.06 g, 21 mmol), potassium fluoride (0.73 g, 13 mmol; 0.6 times the molar quantity of the trifluoropyruvic acid fluoride dimer; spray dried product) and diethylene glycol dimethyl ether (7.48 g, 56 mmol) were charged in a SUS316 30 mL autoclave having a pressure resistance of 10 MPa and cooled to 0° C. using an ice bath. Next, hexafluoropropylene oxide (6.80 g, 41 mmol) was introduced to the autoclave, and stirring was carried out for 20 hours at a temperature of 0° C. When a part of the reaction liquid was sampled and subjected to NMR analysis by means of $^{19}F$ NMR, it was confirmed that the perfluoro(dimethyl-2-oxo-1,4-dioxane) was produced as two diastereomers.

An isomerization step was carried out after the above dimer reaction step. Potassium fluoride was added (0.690 g, 12 mmol; 0.6 times the molar quantity of the trifluoropyruvic acid fluoride dimer (the total quantity of potassium fluoride added was 1.2 times the molar quantity of the trifluoropyruvic acid fluoride dimer); spray dried product), the system was heated to 130° C., and a reaction was carried out for 24 hours. After completion of the reaction, liquid phase was cooled to room temperature, liquid separation was carried out, the upper layer (8.42 g) was subjected to NMR analysis by means of $^{19}F$ NMR using benzotrifluoride as an internal standard substance, and it was confirmed that 0.31 g of perfluoro(2,4-dimethyl-2-fluoroformyl-1,3-dioxolane) (a yield of 3%) had been produced. When the lower layer (10.1 g) was subjected to NMR analysis by means of $^{19}F$ NMR using benzotrifluoride as an internal standard substance, it was confirmed that 0.95 g of perfluoro(2,4-dimethyl-2-fluoroformyl-1,3-dioxolane) had been produced (a yield of 7%) (the combined yield of the upper layer and lower layer was 10% relative to the trifluoropyruvic acid fluoride dimer). It was confirmed that the obtained target product was produced as two diastereomers.

Example 17

Trifluoropyruvic acid fluoride dimer (1.01 g, 3.5 mmol), potassium fluoride (0.021 g, 0.36 mmol; 0.1 times the molar quantity of the trifluoropyruvic acid fluoride dimer; spray dried product) and diethylene glycol dimethyl ether (0.94 g, 7.0 mmol) were charged in a SUS316 30 mL autoclave having a pressure resistance of 10 MPa and cooled to 0° C. using an ice bath. Next, hexafluoropropylene oxide (1.2 g, 7.2 mmol) was introduced to the autoclave, and stirring was carried out for 15 hours at a temperature of 0° C. When a part of the reaction liquid was sampled and subjected to NMR analysis by means of $^{19}F$ NMR, it was confirmed that the perfluoro(dimethyl-2-oxo-1,4-dioxane) was produced as two diastereomers at a yield of 82%.

An isomerization step was carried out after the above dimer reaction step. Potassium fluoride was added (0.312 g, 5.4 mmol; 1.54 times the molar quantity of the trifluoropyruvic acid fluoride dimer (the total quantity of potassium fluoride added was 1.64 times the molar quantity of the trifluoropyruvic acid fluoride dimer); spray dried product) to the autoclave, the system was heated to 80° C. and then to 130° C., and a reaction was carried out for 15 hours. After completion of the reaction, the system was cooled to room temperature, and liquid phase was carried out to obtain an upper layer (a diglyme layer) and a lower layer (a fluorous layer). When the lower layer was subjected to NMR analysis by means of $^{19}F$ NMR using benzotrifluoride as an internal standard substance, it was confirmed that perfluoro(2,4-dimethyl-2-fluoroformyl-1,3-dioxolane) had been produced (0.54 g, 1.74 mmol, a yield of 25% relative to the trifluoropyruvic acid dimer). In addition, when the upper layer and unnecessary substances were dissolved in heavy water and subjected to NMR analysis by means of $^{19}F$ NMR using trifluoroethanol as an internal standard substance, it was confirmed that perfluoro(2,4-dimethyl-1,3-dioxolane-2-carboxylic acid) and/or a potassium salt thereof were produced (3.71 mmol, a yield of 53% relative to the trifluoropyruvic acid dimer).

Example 18

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.9 times the molar quantity of the trifluoropyruvic acid fluoride dimer (the total quantity of potassium fluoride added was 1.0 times the molar quantity of the trifluoropyruvic acid fluoride dimer), and it was confirmed that perfluoro(2,4-dimethyl-2-fluoroformyl-1,3-dioxolane) was produced at a yield of 26% (relative to the trifluoropyruvic acid dimer) and perfluoro(2,4-dimethyl-1,3-dioxolane-2-carboxylic acid) and/or a potassium salt thereof were produced at a yield of 14% (relative to the trifluoropyruvic acid dimer). It was confirmed that the obtained compounds were each produced as two diastereomers.

Example 19

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.72 times the molar quantity of the trifluoropyruvic acid fluoride dimer (the total quantity of potassium fluoride added was 0.82 times the molar quantity of the trifluoropyruvic acid fluoride dimer), and it was confirmed that perfluoro(2,4-dimethyl-2-fluoroformyl-1,3-dioxolane) was produced at a yield of 32% (relative to the trifluoropyruvic acid dimer) and perfluoro(2,4-dimethyl-1,3-dioxolane-2-carboxylic acid) and/or a potassium salt thereof were produced at a yield of 7% (relative to the trifluoropyruvic acid dimer). It was confirmed that the obtained compounds were each produced as two diastereomers.

Example 20

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.4 times the molar quantity of the trifluoropyruvic acid fluoride dimer (the total quantity of potassium fluoride added was 0.5 times the molar quantity of the trifluoropyruvic acid fluoride dimer), and it was confirmed that perfluoro(2,4-dimethyl-2-fluoroformyl-1,3-dioxolane) was produced at a yield of 25% (relative to the trifluoropyruvic acid dimer) and perfluoro(2,4-dimethyl-1,3-dioxolane-2-carboxylic acid) and/or a potassium salt thereof were produced at a yield of 1% (relative to the trifluoropyruvic acid dimer). It was confirmed that the obtained compounds were each produced as two diastereomers.

Example 21

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 1.38 times the molar quantity of the trifluoropyruvic acid fluoride dimer (the total quantity of potassium fluoride added was 1.48 times the molar quantity of the trifluoropyruvic acid fluoride dimer), and cesium fluoride was added as an additive at a quantity corresponding to 0.16 times the molar quantity of the trifluoropyruvic acid fluoride dimer, and it was confirmed that perfluoro(2,4-dimethyl-2-fluoroformyl-1,3-dioxolane) was produced at a yield of 24% (relative to the trifluoropyruvic acid dimer) and perfluoro(2,4-dimethyl-1,3-dioxolane-2-carboxylic acid) and/or a salt (a potassium salt and/or a cesium salt) thereof were produced at a yield of 58% (relative to the trifluoropyruvic acid dimer). It was confirmed that the obtained compounds were each produced as two diastereomers.

Example 22

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.56 times the molar quantity of the trifluoropyruvic acid fluoride dimer (the total quantity of potassium fluoride added was 0.66 times the molar quantity of the trifluoropyruvic acid fluoride dimer), and cesium fluoride was added as an additive at a quantity corresponding to 0.16 times the molar quantity of the trifluoropyruvic acid fluoride dimer, and it was confirmed that perfluoro(2,4-dimethyl-2-fluoroformyl-1,3-dioxolane) was produced at a yield of 33% (relative to the trifluoropyruvic acid dimer) and perfluoro(2,4-dimethyl-1,3-dioxolane-2-carboxylic acid) and/or a salt (a potassium salt and/or a cesium salt) thereof were produced at a yield of 19% (relative to the trifluoropyruvic acid dimer). It was confirmed that the obtained compounds were each produced as two diastereomers.

Example 23

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.31 times the molar quantity of the trifluoropyruvic acid fluoride dimer (the total quantity of potassium fluoride added was 0.41 times the molar quantity of the trifluoropyruvic acid fluoride dimer), and cesium fluoride was added as an additive at a quantity corresponding to 0.082 times the molar quantity of the trifluoropyruvic acid fluoride dimer, and it was confirmed that perfluoro(2,4-dimethyl-2-fluoroformyl-1,3-dioxolane) was produced at a yield of 33% (relative to the trifluoropyruvic acid dimer) and perfluoro(2,4-dimethyl-1,3-dioxolane-2-carboxylic acid) and/or a salt (a potassium salt and/or a cesium salt) thereof were produced at a yield of 8% (relative to the trifluoropyruvic acid dimer). It was confirmed that the obtained compounds were each produced as two diastereomers.

Example 24

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.56 times the molar quantity of the trifluoropyruvic acid fluoride dimer (the total quantity of potassium fluoride added was 0.66 times the molar quantity of the trifluoropyruvic acid fluoride dimer), and tetramethylammonium fluoride was added as an additive at a quantity corresponding to 0.16 times the molar quantity of the trifluoropyruvic acid fluoride dimer, and it was confirmed that perfluoro(2,4-dimethyl-2-fluoroformyl-1,3-dioxolane) was produced at a yield of 37% (relative to the trifluoropyruvic acid dimer) and perfluoro(2,4-dimethyl-1,3-dioxolane-2-carboxylic acid) and/or a salt (a potassium salt and/or a cesium salt) thereof were produced at a yield of 13% (relative to the trifluoropyruvic acid dimer). It was confirmed that the obtained compounds were each produced as two diastereomers.

Example 25

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.9 times the molar quantity of the trifluoropyruvic acid fluoride dimer (the total quantity of potassium fluoride added was 1.0 times the molar quantity of the trifluoropyruvic acid fluoride dimer), and 18-crown-6-ether was added as an additive at a quantity corresponding to 1.0 times the molar quantity of the trifluoropyruvic acid fluoride dimer, and it was confirmed that perfluoro(2,4-dimethyl-2-fluoroformyl-1,3-dioxolane) was produced at a yield of 41% (relative to the trifluoropyruvic acid dimer) and perfluoro(2,4-dimethyl-1,3-dioxolane-2-carboxylic acid) and/or a potassium salt thereof were produced at a yield of 6% (relative to the trifluoropyruvic acid dimer). It was confirmed that the obtained compounds were each produced as two diastereomers.

Example 26

A reaction was carried out under the same conditions as those used in Example 17, except that after perfluoro(dimethyl-2-oxo-1,4-dioxane) was obtained from the trifluoropyruvic acid fluoride dimer at a yield of 82%, the quantity of potassium fluoride added in the isomerization step was changed to a quantity corresponding to 0.4 times the molar quantity of the trifluoropyruvic acid fluoride dimer (the total quantity of potassium fluoride added was 0.5 times the molar quantity of the trifluoropyruvic acid fluoride dimer), and 18-crown-6-ether was added as an additive at a quantity corresponding to 0.5 times the molar quantity of the trifluoropyruvic acid fluoride dimer, and it was confirmed that perfluoro(2,4-dimethyl-2-fluoroformyl-1,3-dioxolane) was produced at a yield of 41% (relative to the trifluoropyruvic acid dimer) and perfluoro(2,4-dimethyl-1,3-dioxolane-2-carboxylic acid) and/or a potassium salt thereof were produced at a yield of 6% (relative to the trifluoropyruvic acid dimer). It was confirmed that the obtained compounds were each produced as two diastereomers.

Comparative Example 1

A reaction was carried out under the same conditions as those used in Example 17, except that the fluoride used in the dimer reaction step was changed to cesium fluoride and the cesium fluoride was added at a quantity corresponding to 0.12 times the molar quantity of perfluoro(dimethyl-2-oxo-1,4-dioxane), and after obtaining perfluoro(dimethyl-2-oxo-1,4-dioxane) from the trifluoropyruvic acid fluoride dimer, a reaction was carried out under the same conditions as those used in Example 17, except that the fluoride used in the isomerization step was changed to cesium fluoride and the quantity of cesium fluoride added was changed to a quantity corresponding to 0.36 times the molar quantity of the trifluoropyruvic acid fluoride dimer (the total quantity of cesium fluoride added was 0.48 times the molar quantity of the trifluoropyruvic acid fluoride dimer), and it was confirmed that perfluoro(2,4-dimethyl-2-fluoroformyl-1,3-dioxolane) was produced at a yield of 37% (relative to the trifluoropyruvic acid fluoride dimer). It was confirmed that the obtained compound was produced as two diastereomers.

According to one aspect of the present invention, perfluoro(2,4-dimethyl-2-fluoroformyl-1,3-dioxolane) can be produced on an industrial scale by using a trifluoropyruvic acid fluoride dimer, which is easy to handle, as a raw material in the presence of potassium fluoride and/or sodium fluoride, which are fluorides that are industrially inexpensive and easy to procure. Perfluoro(2,4-dimethyl-2-fluoroformyl-1,3-dioxolane) produced by the above production method can be used as a synthesis of raw material for poly[perfluoro(2-methylene-4-methyl-1,3-dioxolane)], which is promising as a resin for gas separation membranes, a transparent resin for optical fibers, and the like.

The invention claimed is:

1. A method of producing perfluoro(2,4-dimethyl-2-fluoroformyl-1,3-dioxolane), the method comprising:

reacting a trifluoropyruvic acid fluoride dimer with hexafluoropropylene oxide in an organic solvent in the presence of at least one fluoride selected from the group consisting of potassium fluoride and sodium fluoride, wherein an amount of the at least one fluoride added in the reacting is from 0.08 to 0.3 times of a molar amount the trifluoropyruvic acid fluoride dimer, separating the perfluoro(dimethyl-2-oxo-1,4-dioxane) obtained in the reacting from a reaction liquid, and then conducting isomerization of perfluoro(dimethyl-2-oxo-1,4-dioxane) into perfluoro(2,4-dimethyl-2-fluoroformyl-1,3-dioxolane) in the presence of an organic solvent and the at least one fluoride further added in the isomerization, wherein an amount of the at least fluoride further added in the isomerization is from 0.5 to 1.5 times of a molar amount of the perfluoro(dimethyl-2-oxo-1,4-dioxane), or wherein an amount of the at least one fluoride further added in the isomerization is from 0.5 to 1.8 times of a molar amount of the trifluoropyruvic acid fluoride dimer, wherein at least one additive selected from the group consisting of cesium fluoride and tetramethylammonium fluoride is added in the isomerization, and an amount of the at least one additive in the isomerization is from 0.05 to 0.2 times of a molar amount of the trifluoropyruvic acid fluoride dimer, or an amount of the at least one additive in the isomerization is from 0.03 to 0.15 times of a molar amount of perfluoro(dimethyl-2-oxo-1,4-dioxane).

2. The method of claim 1, wherein the organic solvent is at least one organic solvent selected from the group consisting of ethylene glycol dimethyl ether, diethylene glycol dimethyl ether, triethylene glycol dimethyl ether and tetraethylene glycol dimethyl ether.

3. The method of claim 1, wherein the reacting is carried out in the presence of potassium fluoride.

4. The method of claim 1, wherein the at least one fluoride further added in the isomerization is potassium fluoride.

5. The method of claim 1, wherein the organic solvent in the isomerization is at least one organic solvent selected from the group consisting of ethylene glycol dimethyl ether, diethylene glycol dimethyl ether, triethylene glycol dimethyl ether and tetraethylene glycol dimethyl ether.

6. The method of claim 1, wherein the isomerization is carried out in the presence of potassium fluoride as the at least one fluoride.

7. The method of claim 1, wherein at least one additive selected from the group consisting of a crown ether and a fluoride is further added in the isomerization.

8. A method of producing perfluoro(2,4-dimethyl-2-fluoroformyl-1,3-dioxolane), the method comprising:

reacting a trifluoropyruvic acid fluoride dimer with hexafluoropropylene oxide in an organic solvent in the presence of at least one fluoride selected from the group consisting of potassium fluoride and sodium fluoride, and conducting isomerization of perfluoro(dimethyl-2-oxo-1,4-dioxane) into perfluoro(2,4-dimethyl-2-fluoroformyl-1,3-dioxolane), wherein 18-crown-6 or 15-crown-5 is added as an additive in an amount of from 0.05 to 1.5 times of a molar amount of the trifluoropyruvic acid fluoride dimer in the isomerization.

9. A method of producing perfluoro(2,4-dimethyl-2-fluoroformyl-1,3-dioxolane), the method comprising:

reacting a trifluoropyruvic acid fluoride dimer with hexafluoropropylene oxide in an organic solvent in the presence of at least one fluoride selected from the group consisting of potassium fluoride and sodium fluoride, and conducting isomerization of perfluoro(dimethyl-2-oxo-1,4-dioxane) into perfluoro(2,4-dimethyl-2-fluoroformyl-1,3-dioxolane), wherein 18-crown-6 or 15-crown-5 is added as an additive in the isomerization in an amount of from 0.05 to 1.0 times of a molar amount of perfluoro(dimethyl-2-oxo-1,4-dioxane).

* * * * *